United States Patent
Ibrahim et al.

(10) Patent No.: US 7,751,898 B2
(45) Date of Patent: Jul. 6, 2010

(54) MEDICAL DEVICE WITH MAGNETICALLY-RESPONSIVE CONTROL SWITCH

(75) Inventors: Ibrahim Ibrahim, North Ryde (AU); Peter Single, Lane Cove (AU)

(73) Assignee: Cochlear Limited, Lane Cove (AU)

( * ) Notice: Subject to any disclaimer, the term of this patent is extended or adjusted under 35 U.S.C. 154(b) by 342 days.

(21) Appl. No.: 10/910,591

(22) Filed: Aug. 4, 2004

(65) Prior Publication Data
US 2005/0033383 A1 Feb. 10, 2005

(30) Foreign Application Priority Data
Aug. 4, 2003 (AU) ............... 2003904085

(51) Int. Cl.
*A61N 1/00* (2006.01)
*H01H 9/00* (2006.01)
(52) U.S. Cl. ............... 607/57; 607/60; 335/205
(58) Field of Classification Search ............ 607/16, 607/30, 32, 36, 29, 55–57; 335/205
See application file for complete search history.

(56) References Cited

U.S. PATENT DOCUMENTS

| | | | |
|---|---|---|---|
| 3,397,372 A * | 8/1968 | Maxwell ............... 335/205 |
| 3,571,544 A * | 3/1971 | Sheehan ............... 335/205 |
| 3,778,737 A * | 12/1973 | Bowerman ............... 335/205 |
| 4,124,031 A * | 11/1978 | Mensink et al. ............... 607/31 |
| 4,130,950 A * | 12/1978 | Bazzle et al. ............... 36/127 |
| 4,134,408 A * | 1/1979 | Brownlee et al. ............... 607/33 |
| 4,301,804 A * | 11/1981 | Thompson et al. ............... 607/30 |
| 4,532,930 A | 8/1985 | Crosby et al. |
| 5,948,006 A * | 9/1999 | Mann ............... 607/61 |
| 6,358,281 B1 * | 3/2002 | Berrang et al. ............... 623/10 |
| 6,537,200 B2 | 3/2003 | Leysieffer et al. |
| 6,565,503 B2 | 5/2003 | Leysieffer et al. |
| 6,575,894 B2 | 6/2003 | Leysieffer et al. |
| 6,622,041 B2 * | 9/2003 | Terry et al. ............... 607/9 |
| 6,697,674 B2 | 2/2004 | Leysieffer |
| 2001/0026146 A1 * | 10/2001 | Wuzik et al. ............... 320/127 |
| 2003/0139782 A1 * | 7/2003 | Duncan et al. ............... 607/48 |
| 2004/0073275 A1 * | 4/2004 | Maltan et al. ............... 607/57 |

* cited by examiner

*Primary Examiner*—Mark W Bockelman
(74) *Attorney, Agent, or Firm*—Connolly Bove Lodge & Hutz, LLP

(57) ABSTRACT

In one embodiment of the present invention, an acoustic prosthesis is disclosed. The acoustic prosthesis comprises: an external speech processor unit comprising electronic components and a power source contained within a housing, wherein the power source provides power to the electronic components via a power line; and a magnetically-responsive switch disposed along the power line to switchingly connect the power source to the electronic components in response to the presence of a magnetic field.

19 Claims, 5 Drawing Sheets

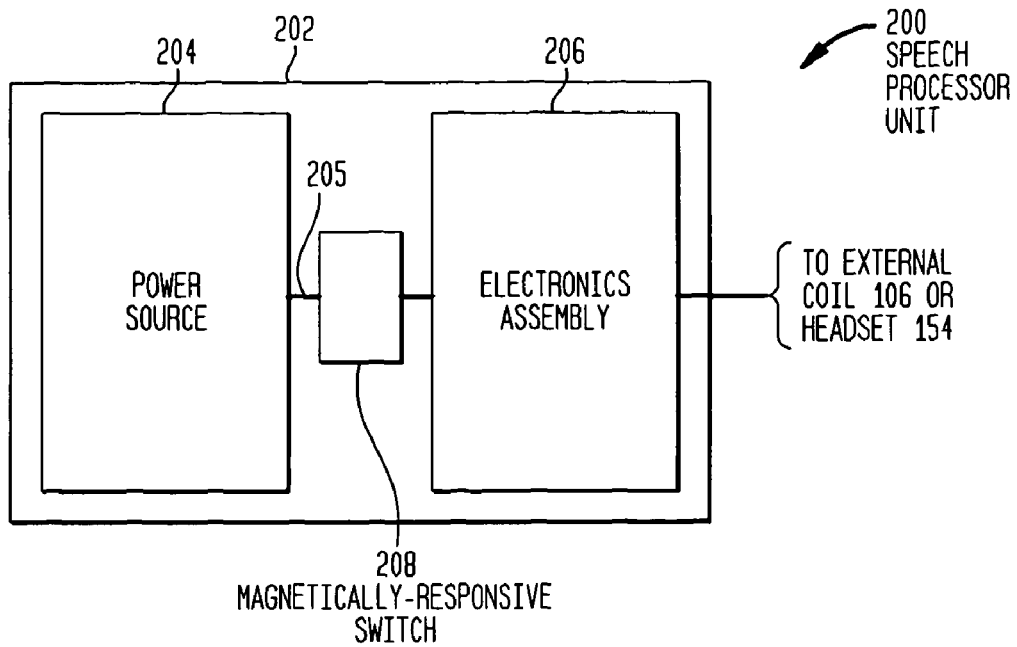
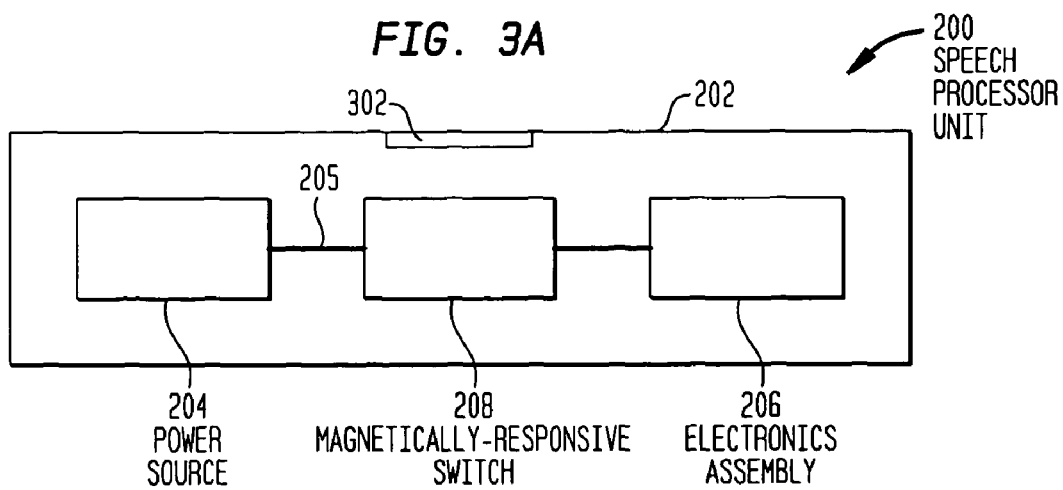
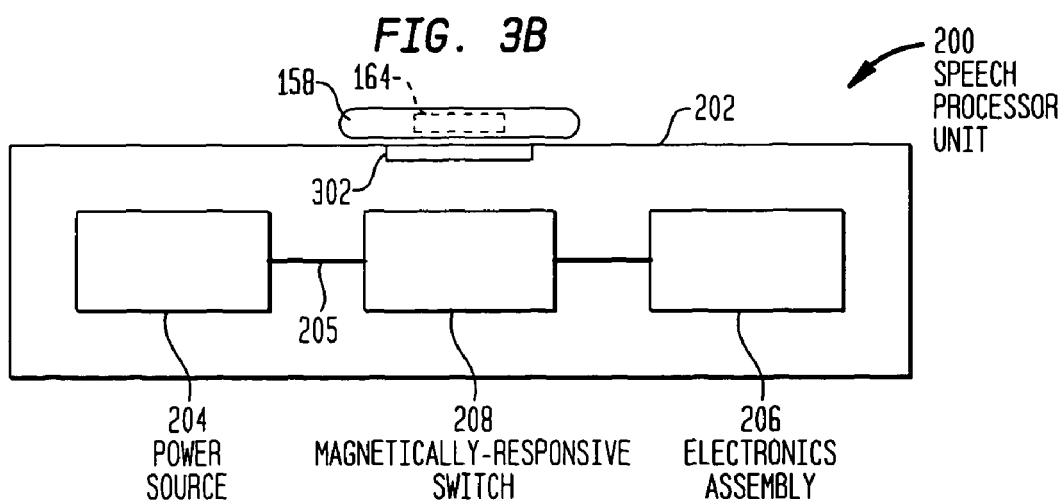

MEDICAL DEVICE WITH MAGNETICALLY-RESPONSIVE CONTROL SWITCH

CROSS-REFERENCE TO RELATED APPLICATIONS

This application claims the priority of Australian Patent No. 2003904085, filed Aug. 4, 2003. The entire disclosure and contents of the above application is hereby incorporated by reference herein.

This application is related to U.S. Pat. Nos. 4,532,930, 6,537,200, 6,565,503, 6,575,894, and 6,697,674. The entire disclosure and contents of the above patents are hereby incorporated by reference herein.

BACKGROUND

1. Field of the Invention

The present invention relates generally to a medical device and, more particularly, to a medical device with a magnetically-responsive control switch.

2. Related Art

The use of medical devices to provide therapy to individuals for various medical conditions has become more widespread as the advantages and benefits such devices provide become more widely appreciated and accepted throughout the population. For example, devices such as acoustic prostheses, implantable pacemakers, defibrillators, organ assist or replacement devices, and other medical devices, have been successful in performing life saving and/or lifestyle enhancement functions for a number of years.

Some medical devices include one or more sensors, processors, controllers, pumps, actuators, or other functional components that are permanently or temporarily implanted in a patient. Many such implantable devices require power and/or require communications with external systems that are part of or operate in conjunction with such implanted components. One common approach to provide for the transcutaneous transfer of power and/or communications with an implantable component is via a transcutaneous transfer system.

One type of implantable medical device that may include a transcutaneous transfer system is an acoustic prosthesis cochlear™ implants provide the benefit of hearing to individuals suffering from severe to profound hearing loss. Hearing loss in such individuals is due to the absence or destruction of the hair cells in the cochlea which transduce acoustic signals into nerve impulses. Cochlear™ implants essentially simulate the cochlear hair cells by directly delivering electrical stimulation to the auditory nerve fibers. This causes the brain to perceive a hearing sensation resembling the natural hearing sensation normally delivered to the auditory nerve.

Conventional cochlear™ implants primarily include external components directly or indirectly attached to the body of the patient (sometimes referred to herein as the recipient), and internal components which are implanted in the patient. The external components typically enable the recipient to control a number of operational settings of the device, through manipulations one or more switches.

For example, the external components often include a speech processor unit that has an on/off switch which is manipulated by a user. Due to its small dimensions, the switch may be difficult to operate particularly for the elderly and disabled. Further, the switch can allow the ingress of moisture into the interior of the speech processor unit resulting in its destruction. The switch can also easily be corroded by moisture rendering it unreliable and unsuitable for use in humid environments. In addition, certain types of switches may be susceptible to breakage resulting from mechanical fatigue.

SUMMARY

In accordance with one aspect of the present invention a medical device is disclosed. The medical device comprises: at least one operational component; and a magnetically-responsive switch to select operational settings of the operational component.

In accordance with another aspect of the present invention an implantable medical device is disclosed. The medical device comprises: an external component, configured to be worn on a patient's body, comprising at least one magnetically-responsive switch to select operational settings of the medical device; and an implantable component communicably coupled to the external component.

In accordance with a further aspect of the invention, an acoustic prosthesis is disclosed. The acoustic prosthesis comprises: an external speech processor unit comprising electronic components and a power source contained within a housing, wherein the power source provides power to the electronic components via a power line; and a magnetically-responsive switch disposed along the power line to switchingly connect the power source to the electronic components in response to the presence of a magnetic field.

BRIEF DESCRIPTION OF THE DRAWINGS

FIG. 2 is a functional block diagram of one embodiment of a speech processor unit of FIG. 1B implementing a magnetically-responsive switch in accordance with one embodiment present invention.

FIG. 3A is a side view of the speech processor unit illustrated in FIG. 2 without the presence of a magnetic field source to activate the magnetically-responsive switch.

FIG. 3B is a side view of the speech processor unit illustrated in FIG. 2 with the presence of a magnetic field source to activate the magnetically-responsive switch.

DETAILED DESCRIPTION

Embodiments of the present invention are directed to a medical device having at least one operational component; and a magnetically-responsive switch to select operational settings of the operational component. Utilization of a magnetically-responsive switch is particularly beneficial for providing an alternate means for controlling the operations of an implantable component of an implantable medical device. Implantable medical devices, as noted, typically comprise one or more external components worn on the body of a patient and one or more internal components temporarily or permanently implanted in the patient.

External components of a medical device are worn on the body of a recipient, often for considerable periods of time and during various activities ranging from the sedentary to the active in a variety of environmental conditions. The external, patient-worn components often include one or more switches controlled by the operator to select certain operational settings of the device. At times it may be necessary to reliably and quickly activate the switch. However, due to their small dimensions, such switches can be difficult to operate, particularly for the elderly and disabled. The switch may be corroded by moisture due to exposure to humidity, sweat, rain and the like. In addition, certain types of switches may be susceptible to failure resulting from mechanical fatigue, ingress of dirt or other foreign particles that interfere with the proper operation of the switch. Utilization of an embodiment of a magnetically-responsive switch of the present invention provides an alternate means for quickly and reliably selecting operational settings of the medical device when the user-operable switches are unavailable.

Embodiments of the present invention are described below in connection with one embodiment of an exemplary implantable medical device, an acoustic prosthesis (also referred to as a cochlear™ prosthesis, cochlear™ implant system, hearing prosthetic device, cochlear™ prosthetic device and the like). Cochlear™ prostheses use direct electrical stimulation of auditory nerve cells to bypass absent or defective hair cells that normally transducer acoustic vibrations into neural activity. Such prostheses generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a cochlear™ prosthetic device provides stimulation of the cochlear nucleus in the brainstem.

Figure 1A:
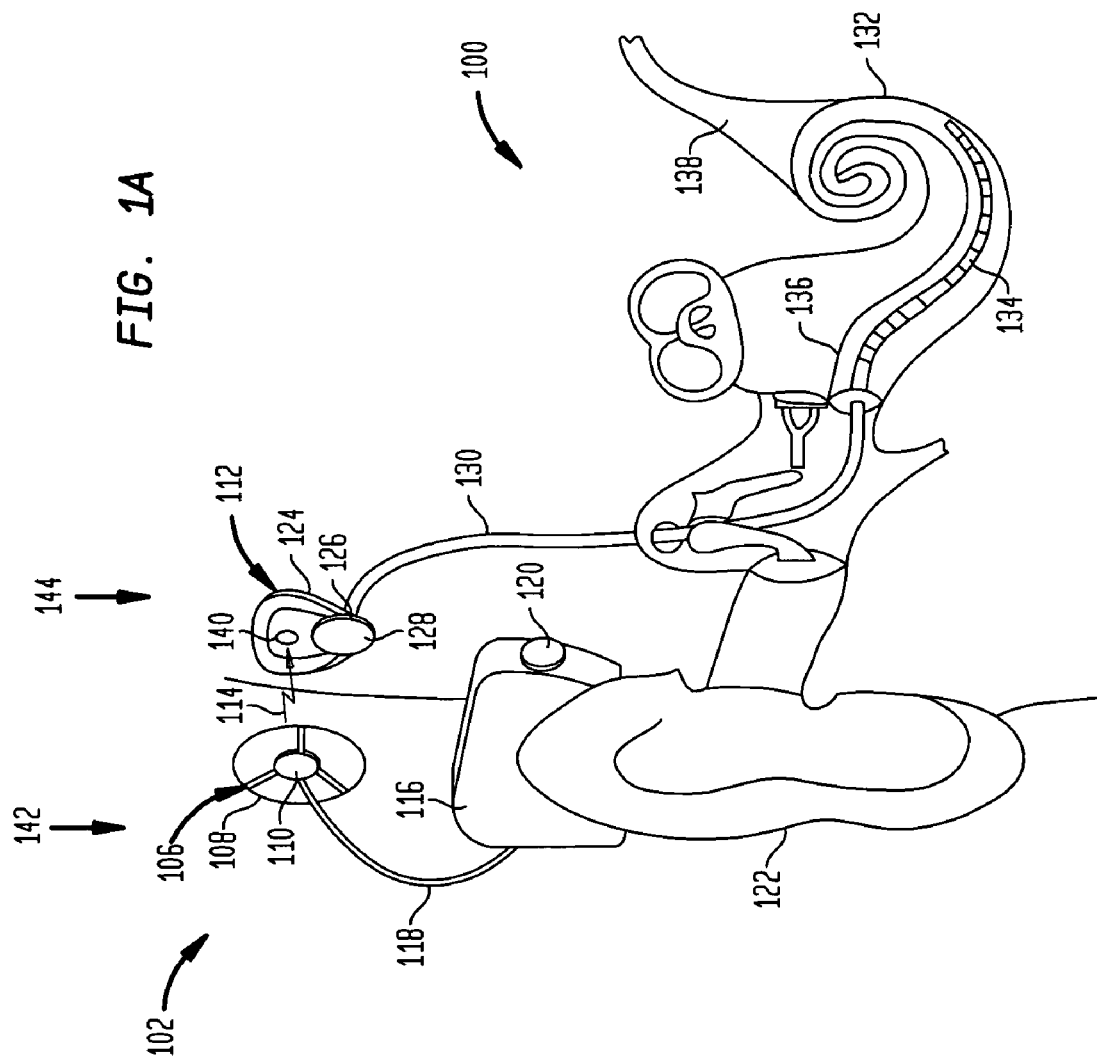
FIG. 1A is a schematic block diagram of one embodiment of an exemplary acoustic prosthesis suitable for implementing embodiments of the present invention.

Exemplary cochlear™ prostheses in which the present invention may be implemented include, but are not limited to, those systems described in U.S. Pat. Nos. 4,532,930, 6,537,200, 6,565,503, 6,575,894 and 6,697,674, which are hereby incorporated by reference herein. FIG. 1A is a schematic diagram of an exemplary cochlear™ implant system 100 in which embodiments of the present invention may be implemented. Cochlear™ implant system 100 comprises external components 142 which are directly or indirectly attached to the body of the recipient, and internal components 144 which are temporarily or permanently implanted in the recipient. External components 142 typically comprise a microphone 120 for detecting sounds, a speech processor 116 that converts the detected sounds into a coded signal, a power source (not shown), and an external transmitter unit 106. External transmitter unit 106 comprises an external coil 108 and a magnet 110 secured directly or indirectly to external coil 108. Speech processor 116 processes the output of microphone 120 that is positioned, in the depicted embodiment, on the ear 122 of the recipient. Speech processor 116 generates a coded signal which is provided to external transmitter unit 106 via cable 118.

Internal components 144 comprise an internal receiver unit 112, a stimulator unit 126, and an electrode array 134. Internal receiver unit 112 comprises an internal receiver coil 124 and a magnet 140 fixed relative to internal coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to the basilar membrane 136 thereby stimulating the auditory nerve 138.

Collectively, transmitter antenna coil 108 (or more generally, external coil 108) and receiver antenna coil 124 (or, more generally internal coil 124) form an inductively-coupled coil system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone molding (not shown). In use, implantable receiver unit 112 can be positioned in a recess of the temporal bone adjacent ear 122 of the recipient.

Implantable receiver unit 112 has a magnet 140 embedded within the silicone housing of internal coil 124 to allow transcutaneous alignment of external coil 108 of external transmitter unit 106 and internal coil 124 of internal receiver unit 112. This magnetic transcutaneous alignment provides an attraction force that is designed to maintain external coil 108 in place on the head of the recipient without the necessity for any additional clips or other holding means. This magnetic transcutaneous alignment also facilitates the correct lateral alignment of external coil 108 over internal coil 124 to permit the efficient transmission of power and/or data.

Figure 1B:
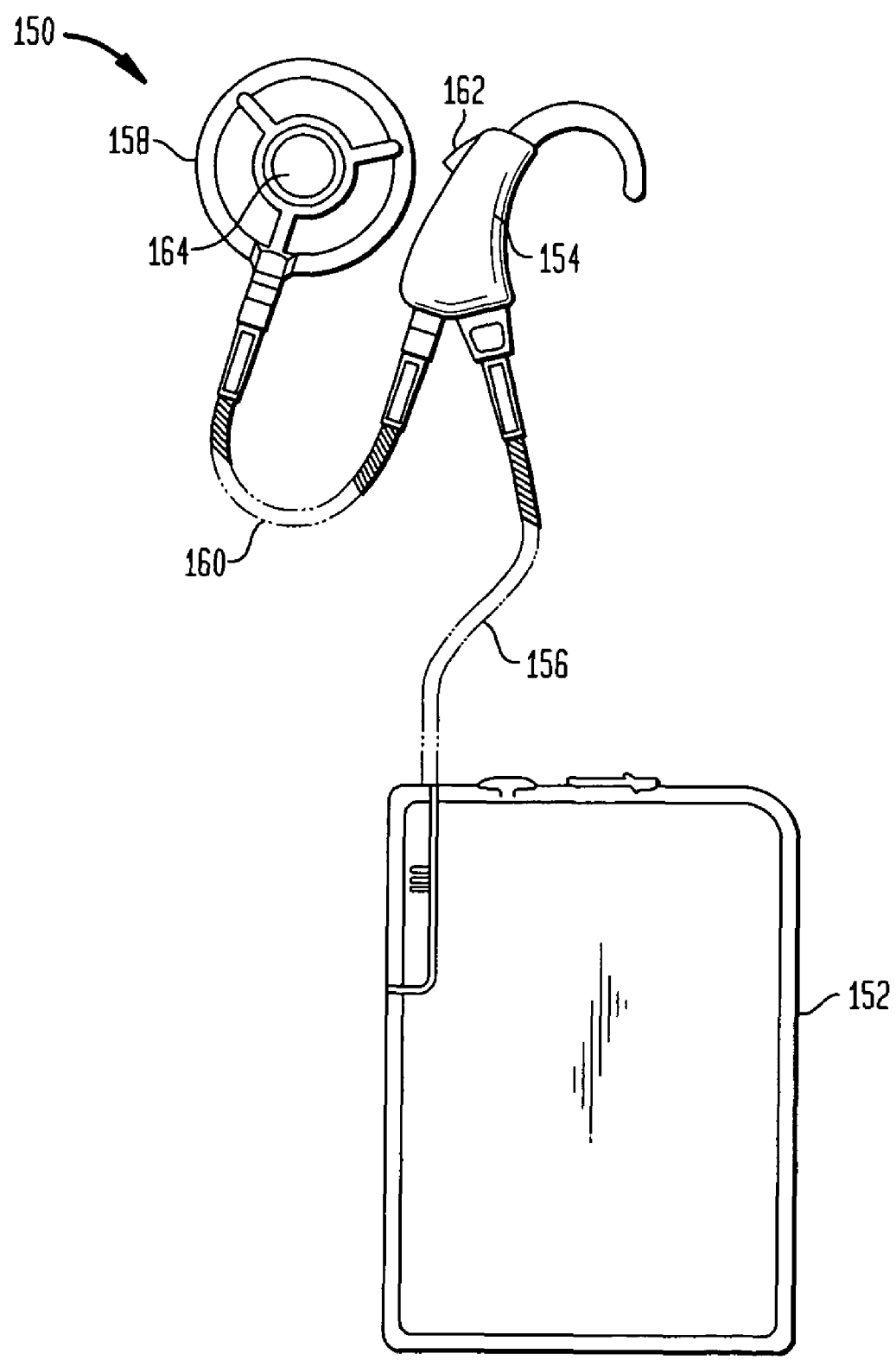
FIG. 1B is a schematic block diagram of an alternative embodiment of an exemplary acoustic prosthesis suitable for implementing embodiments of the present invention.

External assembly 142 of cochlear™ implant system 100 may have different configurations and arrangements. FIG. 1B is a perspective view of one embodiment of external assembly 142, referred to as external assembly arrangement 150. In arrangement 150, a body-worn speech processing unit 152 is connected to a headset unit 154 with a first cable 156. Headset unit 154 is, in turn, connected to a transmitter coil 158 with a second cable 160.

In this exemplary embodiment, headset unit 154 comprises three audio pickup devices 162. In one embodiment, audio pickup devices 162 are microphones, although in alternative embodiments audio pickup devices 162 can be telecoils or other similar devices now or later developed. Each audio pickup device 162 detects and converts ambient sound into an electrical audio signal. The electrical audio signals are transmitted over cable 156 to speech processing unit 152, which contains appropriate speech processing circuitry to convert the electrical audio signals into electrical coded stimulation signals according to a particular speech processing strategy. The stimulation signals are transmitted via cable 156 from speech processing unit 152 to headset unit 154, and from headset unit 154 to external coil 158 via cable 160, for transmission over an RF link to implanted stimulator unit 126 (FIG. 1).

FIG. 2 is an architectural block diagram of one embodiment of a speech processor unit such as external speech processor unit 116 of FIG. 1A and external speech processor unit 152 of FIG. 1B. In FIG. 2, the illustrative speech processor unit is referred to as speech processor unit 200.

Speech processor unit 200 is a body worn device, as illustrated in FIGS. 1A and 1B, and comprises an electronics assembly 206 implementing functionality of the above-noted speech processor unit, and a power source 204 that supplies power to electronics assembly 206 via power line 205. Speech processor unit 12 includes a control switch 208 in power line 205 that switchingly connects power source 204 to electronics assembly 206. In accordance with the teachings of the present invention, switch 208 is a magnetically-responsive switch. The magnetically-responsive switch is actuated with the presence or absence of a magnetic field. In one exemplary embodiment, for example, switch 208 has a set of one or more normally closed contacts (not shown). In the presence of a magnetic field, the contacts open, breaking the supply of power from power supply 204 to electronic assembly 206. When this occurs, speech processor unit 200 becomes inoperative.

FIGS. 3A and 3B are side views of speech processor unit 200. In FIG. 3A, a magnetic field source is not present to activate magnetically-responsive switch 204; in FIG. 3B, such a magnetic field source is present to activate magnetically-responsive switch 204. In the embodiment shown, the magnetic field source is magnet 164 housed in external coil 158.

In this particular embodiment, speech processor unit 200 further comprises a mounting formation 302 to detachably secure magnetic field source 164 to an exterior surface of housing 202. Such a mounting formation 302 can be implemented to mechanically or otherwise secure a magnetic field source to housing 202. In one embodiment, mounting formation 302 is a magnetic mounting formation. In one specific implementation, magnetic mounting formation 302 is comprised of ferromagnetic material such as an iron disk. Mounting formation 302 may be dimensioned as is suitable for a given application given, for example, the orientation of speech processor unit 200, the mass of the magnetic field source 164 and associated elements, such as coil 158, the size of the magnetic field source, and other factors.

In the embodiment illustrated in FIGS. 3A and 3B, mounting formation 302 is secured to an interior surface of housing 202. It should be appreciated, however, that mounting formation 302 may be secured to the exterior surface of housing 202, or in the wall of housing 202. Regardless, mounting formation 302 is located in housing 202 so that when magnetic field source 164 is detachably secured to housing 202, the magnetic field source is sufficiently proximate to magnetically-responsive switch 208 such that a magnetic field generated by said magnetic field source 164 activates switch 208.

In operation, magnetically responsive switch 208, as noted, is closed; that is, power is supplied from power source 204 to electronics assembly 206. Should the recipient want to turn off cochlear™ implant system 100 and is otherwise unable to do so quickly, reliably or easily, the recipient can place external coil 158 over speech processor unit 200 so that magnet 164 of transmitting coil 158 is magnetically attached to housing 202 juxtaposed with mounting formation 302. Magnetic mounting formation 302 and magnet 164 provide sufficient magnetic force to maintain coil 158 secured to the exterior surface of housing 202.

When in this position, a magnetic field generated by magnet 164 causes the contacts (not shown) of magnetically-responsive switch 208 to open, removing power from electronics assembly 206. This, in turn, causes the power applied to implanted assembly 144 (FIG. 1) ceases, causing internal assembly 144 to cease operating.

Conversely, when it is desired to use implant 100, transmitting coil 158 is removed from magnetic mounting formation 302. When this occurs, the contacts of magnetically-responsive switch 208 close and power is supplied from power source 204 to electronics assembly 206 and, as a result, to internal component 144.

In one embodiment, magnetically-responsive switch 208 is a reed switch. In general, reed switches respond to the presence or absence of a magnetic field. Accordingly, all that is required is for the user to place a magnetic field source in proximity to the switch to cause the switch to open, and to remove the magnetic field source to cause the switch to close. FIGS. 4A to 4F are exemplary implementations of a reed switch which can used in accordance with the teachings of the present invention. Some of these embodiments require more elaborate movement of the magnetic field source than others, which may be beneficial in some embodiments. However, it is preferred that a more simple movement be required to facilitate ease of use of the medical device.

Figure 4A:
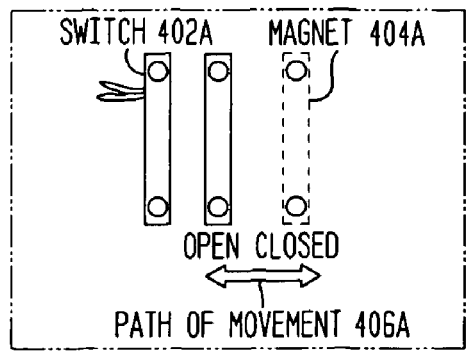
FIGS. 4A-4F are schematic views of different embodiments of a reed switch to implement the magnetically-responsive switch illustrated in FIG. 2.

In FIG. 4A, a read switch 402A is activated in response to perpendicular motion of magnet 404A, as shown by the path of movement 406A. Here, reed switch 402A opens when magnet 404 travels from closed position distant from switch 402A to an open position proximate to switch 402A. As long as magnet 404A is retained at or near the noted open position along path 406A, reed switch 402A will remain open.

Figure 4B:
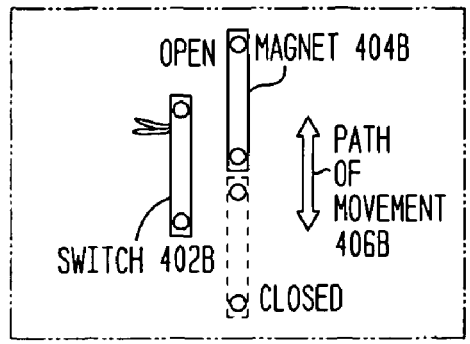

In FIG. 4B, a read switch 402B is activated in response to parallel motion of magnet 404B from one position in which switch 402B is closed to another position in which switch 402B is open, as shown by the path of movement 406B. Thus, as long as magnet 404B is retained along path 406B, reed switch 402B will remain open.

Figure 4C:
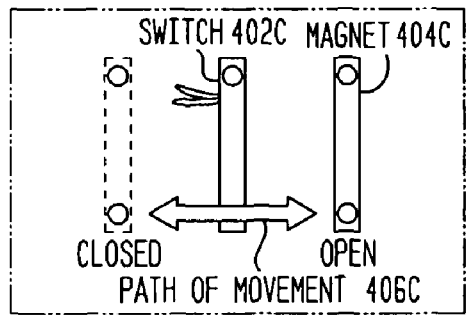

In FIG. 4C, a read switch 402C is activated in response to front-to-back motion of magnet 404C, as shown by the path of movement 406C. This motion is similar to that sown in FIG. 4B, except that this motion is at right angles to switch 402C, and magnet 404C is to completely pass switch 404C. Thus, in this embodiment, it may be preferable to identify path of movement 404C on the exterior surface 222 of housing 202. In addition, mounting formation 302 is to be positioned relative to switch 404C as illustrated by the "open" position shown in FIG. 4C. Thus, as long as magnet 404C transitions through path of movement 404C and is retained at the illustrated open position, reed switch 402C will remain open.

Figure 4D:
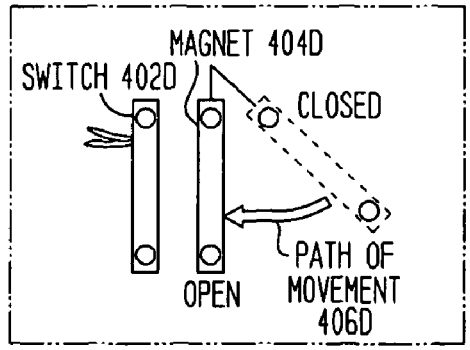

In FIG. 4D, a read switch 402D is activated in response to a pivotal motion of magnet 404D, as shown by the path of movement 406D.

Figure 4E:
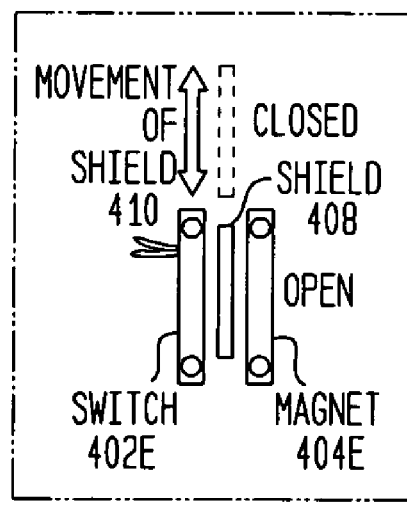

In FIG. 4E, a magnet 404E is permanently fixed relative to switch 402E. The switch 402E will open and close in response to the presence and absence of a shield 408 of magnetic material between magnet 404E and switch 402E, as shown by path 410.

Figure 4F:
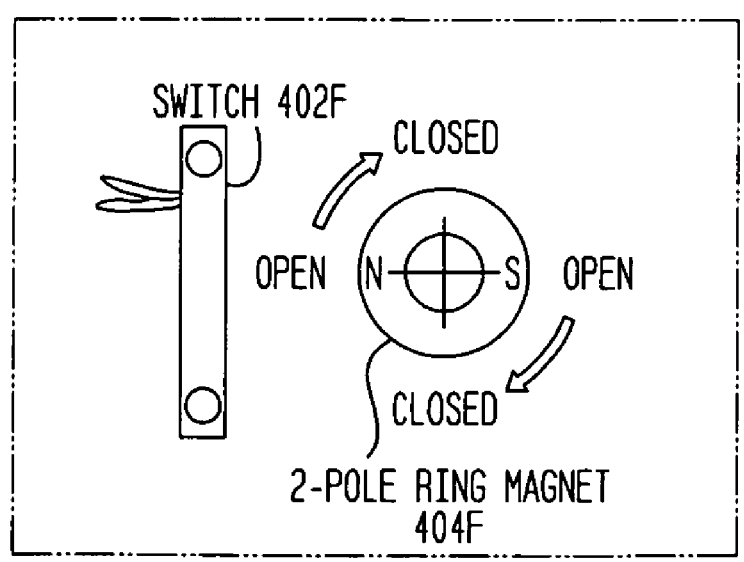

In FIG. 4F, when a magnetic pole axis and the switch 402F axis are parallel, the switch 402F closes. When the axes are perpendicular, switch 402F opens. Accordingly, rotation of ring magnet 404F will cause switch 402F to open and close as indicated.

As one of ordinary skill in the art would find apparent, the above and other types of reed switches may be implemented in the present invention. Reed switches such as those described above are commercially available from Reed Switch Development Corporation, Racine, Wis.

It should also be apparent to those of ordinary skill in the art that other magnetically-responsive switches can be used. For example, in one alternative embodiment, magnetically-responsive switch 204 is a Hall-effect device. In another alternative embodiment, magnetically-responsive switch 204 is an LC oscillator. In this latter embodiment, the oscillator may be designed such that the resonant frequency changes with the presence of the magnetic field. In one particular embodiment, a piece of magnetic material is included in the inductor of the oscillator. The magnetic material has a low hysteresis and saturates in the presence of a magnetic field. Consequently, the inductance is caused to change resulting in the oscillator's resonance frequency shifting. This shift is detected and is used to operate switch contacts.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A medical device, comprising:
    an operational component comprising:
        a housing;
        a magnetically-responsive switch at least partially mounted in said housing configured to select an operational status of said operational component in response to a presence of a magnetic field;
        a mounting formation secured to one of either an interior surface or an exterior surface of a wall of said housing proximate to said magnetically-responsive switch, wherein the mounting formation is configured to allow a person to magnetically secure a source of said magnetic field to an exterior surface of said housing while the medical device is operational; and
        a transcutaneous transfer system including an external coil connected to said housing and an implantable coil communication with said external coil.

2. The medical device of claim 1, wherein said operational component comprises:
    an external component; and
    an implantable component communicably coupled to said external component.

3. The medical device of claim 2, wherein said magnetically-responsive switch controls an operational status of said implantable component.

4. The medical device of claim 1, wherein said magnetically-responsive switch controls application of power to one or more components of the medical device.

5. The medical device of claim 1, wherein said magnetically-responsive switch comprises one of a group consisting of:
    a reed switch;
    a Hall-effect switching device; and
    an LC oscillator having a resonant frequency that changes with the presence and absence of a magnetic field.

6. The medical device of claim 1, wherein said medical device is an acoustic prosthetic device comprising:
    an external speech processor;
    an internal stimulator unit;
    wherein said transcutaneous transfer system facilitates transcutaneous transmission of signals from said speech processor to said stimulator unit.

7. The medical device of claim 1, wherein each of said coils comprises one of a pair of alignment magnets, further wherein said magnetic field is generated by said alignment magnet of said external coil when said external coil is positioned in electromagnetic proximity to said magnetically-responsive switch.

8. The medical device of claim 1, wherein said mounting formation comprises a magnetic mounting formation.

9. The medical device of claim 8, wherein said magnetic mounting formation comprises ferromagnetic material secured to said housing.

10. The medical device of claim 9, wherein said ferromagnetic material comprises an iron disc.

11. A medical device, comprising:
    an implantable component configured to be implanted in a recipient of the medical device; and
    an external component comprising:
        a housing;
        a magnetically-responsive switch at least partially mounted in said housing, wherein the switch is configured to select an operational status of one or more components of the medical device in response to a presence of a magnetic field;
        a mounting formation secured to one of either an interior surface or an exterior surface of a wall of said housing proximate to said magnetically-responsive switch, wherein the mounting formation is configured to allow a person to magnetically secure a source of said magnetic field to an exterior surface of said housing while the medical device is operational;
        a transcutaneous transfer system coupling the external component to the implantable component, the system including an external coil and an implantable coil.

12. The medical device of claim 11, wherein said magnetically-responsive switch controls an operational status of said implantable component.

13. The medical device of claim 11, wherein said magnetically-responsive switch controls application of power to one or more components of the medical device.

14. The medical device of claim 11, wherein said magnetically-responsive switch comprises one of a group consisting of:
    a reed switch;
    a Hall-effect switching device; and
    an LC oscillator having a resonant frequency that changes with the presence and absence of a magnetic field.

15. The medical device of claim 11, wherein said medical device is an acoustic prosthetic and wherein said external component comprises a speech processor, and wherein said implantable component comprises an internal stimulator unit, and wherein said transcutaneous transfer system facilitates transcutaneous transmission of signals from said speech processor to said stimulator unit.

16. The medical device of claim 11, wherein each of said coils comprises one of a pair of alignment magnets, further wherein said magnetic field is generated by said alignment magnet of said external coil when said external coil is positioned in electromagnetic proximity to said magnetically-responsive switch.

17. The medical device of claim 11, wherein said mounting formation comprises a magnetic mounting formation.

18. The medical device of claim 17, wherein said magnetic mounting formation comprises ferromagnetic material secured to said housing.

19. The medical device of claim 18, wherein said ferromagnetic material comprises an iron disc.

* * * * *